United States Patent [19]

Sano et al.

[11] Patent Number: 5,286,888
[45] Date of Patent: Feb. 15, 1994

[54] RUTHENIUM-PHOSPHINE COMPLEX AND PROCESS FOR PRODUCING OPTICALLY ACTIVE 1-SUBSTITUTED-1,3-PROPANEDIOLS USING THE SAME AS A CATALYST

[75] Inventors: Noboru Sano; Noboru Sayo; Hidenori Kumobayashi, all of Tokyo, Japan

[73] Assignee: Takasago International Corporation, Tokyo, Japan

[21] Appl. No.: 964,904

[22] Filed: Oct. 22, 1992

[30] Foreign Application Priority Data

Oct. 22, 1991 [JP] Japan .................. 3-274008

[51] Int. Cl.$^5$ .................. C07F 15/00; C07F 9/50
[52] U.S. Cl. .................. 556/21; 556/23; 568/861
[58] Field of Search .................. 556/21, 23; 558/156; 568/861

[56] References Cited

U.S. PATENT DOCUMENTS

| | | | |
|---|---|---|---|
| 4,739,084 | 4/1988 | Takaya et al. | 556/21 |
| 4,739,085 | 4/1988 | Takaya et al. | 556/21 |
| 4,994,590 | 2/1991 | Takaya et al. | 556/21 |
| 5,012,002 | 4/1991 | Kumobayashi et al. | 556/21 |
| 5,144,050 | 9/1992 | Chan et al. | 556/21 |

FOREIGN PATENT DOCUMENTS

55-61937  10/1980  Japan .................. 556/22

OTHER PUBLICATIONS

*J. Chem. Soc., Chem. Commun.*, 1985; 922–924.
*J. Org. Chem.*, 1988; 53, 4081–4084.

Primary Examiner—Werren B. Lone
Attorney, Agent, or Firm—Sughrue, Mion, Zinn, Macpeak & Seas

[57] ABSTRACT

A ruthenium-phosphine complex is disclosed, represented by formula (I):

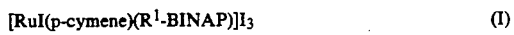

$$[RuI(p\text{-cymene})(R^1\text{-BINAP})]I_3 \qquad (I)$$

where $R^1$-BINAP represents a tertiary phosphine represented by formula (II):

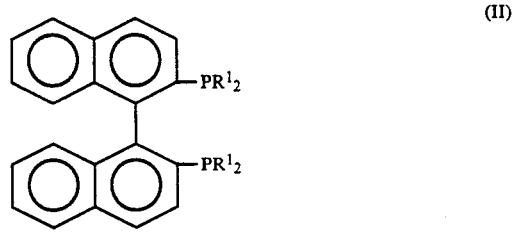

(II)

wherein $R^1$ represents a phenyl group which may be substituted with a lower alkyl group or a halogen atom at the p-position and/or m-position. A process for producing an optically active 1-substituted-1,3-propanediol is also disclosed, comprising hydrogenating a 3-substituted-3-oxopropanol or 3-substituted-3-oxopropanal in the presence of the ruthenium-phosphine complex of formula (I).

8 Claims, No Drawings

RUTHENIUM-PHOSPHINE COMPLEX AND PROCESS FOR PRODUCING OPTICALLY ACTIVE 1-SUBSTITUTED-1,3-PROPANEDIOLS USING THE SAME AS A CATALYST

FIELD OF THE INVENTION

The present invention relates to a ruthenium-phosphine complex useful as a catalyst for various organic synthetic reactions, particularly enantioselective hydrogenation reactions and to a process for producing optically active 1-substituted-1,3-propanediols using the same.

BACKGROUND OF THE INVENTION

A large number of organic synthetic reactions using a transition metal complex as a catalyst have hitherto been developed and made use of for various purposes. In particular, many reports have been made on enantioselective catalysts used for enantioselective synthetic reactions, such as enantioselective hydrogenation and enantioselective isomerization. Among them, metal complexes in which an optically active tertiary phosphine compound is coordinated to metallic rhodium or ruthenium are well known as catalysts for enantioselective hydrogenation reactions.

For example, a rhodium-phosphine complex using 2,2'-bis(diphenylphosphino)-1,1'-binaphthyl (hereinafter abbreviated as BINAP) as a ligand is disclosed in JP-A- 55-61937 (the term "JP-A" as used herein means an "unexamined published Japanese patent application").

With regard to ruthenium, ruthenium complexes obtained by using BINAP or 2,2'-bis(di-p-tolylphosphino)-1,1'-binaphthyl (hereinafter abbreviated as Tol-BINAP) as a ligand, such as $Ru_2Cl_4(BINAP)_2NEt_3$ (wherein Et represents an ethyl group) and $Ru_2Cl_4(Tol-BINAP)_2NEt_3$ have been reported (Ikariya et al., *J. Chem. Soc., Chem. Commun.*, p. 922 (1985)). Also, $Ru(O_2CR^4)_2$(BINAP) and $Ru(O_2CR^4)_2$ (Tol-BINAP) (wherein $R^4$ represents a lower alkyl group or a lower alkyl-substituted phenyl group) have been disclosed in JP-A-62-265293; and $[RuH_l(R^5-BINAP)_m]Z_n$ (wherein $R^5$ represents a hydrogen atom or a methyl group; Z represents $ClO_4$, $BF_4$, or $PF_6$; when l is 0, then m represents 1, and n represents 2; and when l is 1, then m represents 2, and n represents 1) has been disclosed in JP-A-63-41487. However, these ruthenium complexes were complicated in their preparation and had such disadvantages as low yield and poor stability.

Furthermore, JP-A-2-191289 has reported $[RuX_l(S)_m(R^6-BINAP)]Y_n$ (wherein $R^6$ represents a hydrogen atom or a methyl group; X represents a halogen atom; S represents benzene which may be substituted or acetonitrile; Y represents a halogen atom, $ClO_4$, $PF_6$, $BPh_4$ (wherein Ph represents a phenyl group), or $BF_4$; in the case where S is benzene which may be substituted, l is 1, m is 1, and n is 1; and in the case where S is acetonitrile, when l is 1, then m is 2, and n is 1, and when l is 0, then m is 4, and n is 2). However, even when these phosphine complexes are used, there were sometimes problems in their practical applications on an industrial scale, such as insufficiency in catalytic activity, duration, and enantioselectivity depending on the reactions and reaction substrates.

On the other hand, optically active 1-substituted-1,3-propanediols are useful intermediates in enantioselective synthesis for the production of pharmaceuticals, liquid crystal compounds, and natural products. Among these, as a production method of optically active 1-phenyl-1,3-propanediol which is useful as an intermediate of pharmaceuticals such as fluoxetine and tomoxetine, a method in which cinnamyl alcohol is subjected to enantioselective epoxidation to obtain optically active epoxycinnamyl alcohol, which is then reduced by Red-Al (sodium bis(2-methoxyethoxy)aluminum hydride) is reported (Y. Gao, et al., *J. Org. Chem.*, 53, pp. 4081–4084 (1988)). In the above method, however, not only Red-Al which is difficult to handle is employed, but products having a satisfactorily high optical purity cannot be obtained.

SUMMARY OF THE INVENTION

Accordingly, an object of the present invention is to provide a catalyst having high catalytic activity and long duration and capable of giving high enantioselectivity in enantioselective reactions, that is, producing products having a high optical purity. In addition, another object of the present invention is to provide a useful production process of optically active 1-substituted-1,3 propanediols which are important as an intermediate for synthesis of, for example, pharmaceuticals.

Under these circumstances, the present inventors have conducted extensive studies on catalysts having higher activities. As a result, it has been found that certain ruthenium-phosphine complexes having four iodine atoms coordinated therewith have much higher catalytic activities and longer duration than complexes having a lower number of iodine atoms coordinated therewith and that complexes having optically inactive ligands can be used as catalysts for ordinary syntheses, whereas those having optically active ligands can be used as catalysts for enantioselective syntheses, and in particular, when they are used for enantioselective hydrogenation reactions of 3-oxopropanols or 3-oxopropanals, 1-substituted-1,3-propanediols having a high optical purity can be obtained in high yield. The present invention has been completed based on these findings.

The present invention relates to a ruthenium-phosphine complex represented by formula (I):

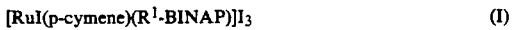

$$[RuI(p\text{-cymene})(R^1\text{-BINAP})]I_3 \qquad (I)$$

wherein $R^1$-BINAP represents a tertiary phosphine represented by formula (II):

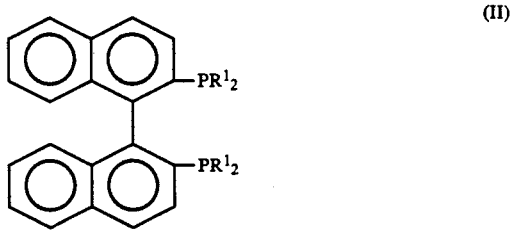

(II)

wherein $R^1$ represents a phenyl group which may be substituted with a lower alkyl group or a halogen atom at the p-position and/or m-position.

The present invention also relates to a process for producing an optically active 1-substituted-1,3-propanediol represented by formula (III):

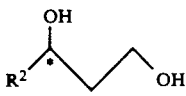

wherein $R^2$ represents a lower alkyl group or a phenyl group which may have a substituent group, and * designates an asymmetric carbon atom, which comprises hydrogenating a 3-substituted 3-oxopropanol or 3-substituted-3-oxopropanal represented by formula (IV):

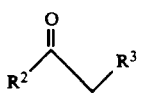

wherein $R^2$ is as defined above, and $R^3$ represents —CHO or —CH$_2$OH, in the presence of a ruthenium-phosphine complex represented by formula (I) having an optically active tertiary phosphine coordinated therewith as a ligand.

DETAILED DESCRIPTION OF THE INVENTION

In the ruthenium-phosphine complex represented by formula (I) of the present invention, $R^1$ represents a phenyl group which may be substituted with a lower alkyl group or a halogen atom at the p-position and/or m-position, and specific examples thereof include a phenyl group, a p-tolyl group, an m-tolyl group, a p-tertbutylphenyl group, a 3,5-dimethylphenyl group, a p-chlorophenyl group, and 3,5-dichlorophenyl group.

The ruthenium-phosphine complex (I) of the present invention can be prepared, for example, according to the following reaction scheme in which a ruthenium-phosphine complex of formula (V) as described in JP-A-2-191289 is reacted with iodine:

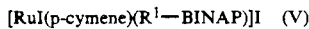
[RuI(p-cymene)(R$^1$—BINAP)]I   (V)
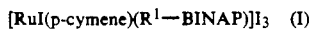
[RuI(p-cymene)(R$^1$—BINAP)]I$_3$   (I)

wherein R$^1$-BINAP is as defined above.

This reaction is carried out with stirring in a suitable solvent such as methanol at 15° to 30° C. for 1 to 5 hours.

Though the ruthenium-phosphine complex (I) of the present invention can be isolated and then used, it can be used as a catalyst for enantioselective synthesis, etc. while mixing the starting complex (V) and iodine to generate it in the reaction mixture. In this case, the amount of iodine added is from 1 to 10 mole, and preferably from 2 to 4 mole per mole of the starting complex (V).

The thus obtained ruthenium-phosphine complex (I) of the present invention can be used as a catalyst of various organic synthetic reactions. When a complex comprising an optically active tertiary phosphine as R$^1$-BINAP is used, it is particularly useful as a catalyst of enantioselective synthetic reactions such as enantioselective hydrogenation. In the case of enantioselective hydrogenation, for example, the complex (I) of the present invention exhibits about 10 times the catalytic activity of the complex (V) as disclosed in JP-A-2-191289.

Next, the process for producing a 1-substituted-1,3-propanediol by using the complex (I) of the present invention as an enantioselective hydrogenation catalyst is explained. This producing process is illustrated by the following reaction scheme:

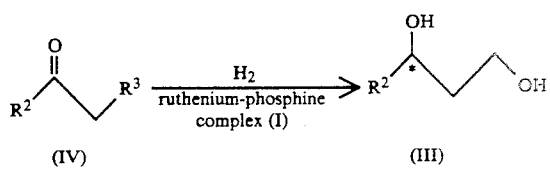

wherein $R^2$ and $R^3$ are as defined above.

In the above reaction scheme, $R^2$ of the compound (IV) represents a lower alkyl group or a phenyl group which may have a substituent group. Specific examples of the lower alkyl group include a methyl group, an ethyl group, a propyl group, a butyl group, an isopropyl group, and a tert-butyl group; and specific examples of the phenyl group which may have a substituent group include a phenyl group, an m-tolyl group, a p-tolyl group, a p-chlorophenyl group, a p-methoxyphenyl group, and a 3,4,5-trimethoxyphenyl group.

As the starting compound (IV) of the present reaction, 3-substituted-3-oxopropanols and 3-substituted-3-oxopropanals can be used. These compounds can be synthesized, for example, as follows.

(1) Synthesis of 3-Substituted-3-oxopropanal (IVa):

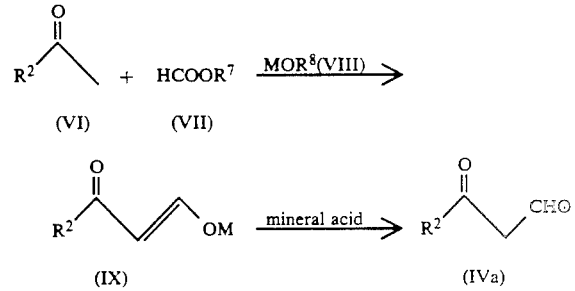

In the above reaction scheme, $R^2$ is as defined above; $R^7$ and $R^8$, which may be the same or different, each represents a lower alkyl group; and M represents lithium, sodium, or potassium.

That is, the ketone (VI) is condensed with the lower formic acid eater (VII) by using the metallic alkoxide (VIII) to obtain the compound (IX), which is then neutralized with a mineral acid to produce the aldehyde (IVa).

(2) Synthesis of 3-Substituted-3-oxopropanol (IVb):

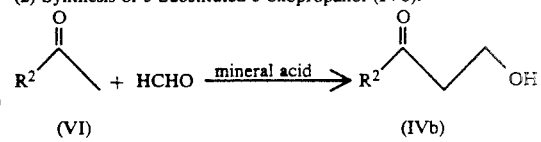

In the above reaction scheme, $R^2$ is as defined above.

That is, the alcohol (IVb) can be synthesized by condensing the ketone (VI) and formaldehyde with a mineral acid as a catalyst.

With respect to the ruthenium-phosphine complex (I) to be used in an enantioselective hydrogenation reaction of the present invention, a complex having an optically active ligand R[1]-BINAP, i.e., the (R)- or (S)-compound, can be used. In this case, final products having a desired absolute configuration can be obtained depending on the selection. Such a ruthenium-phosphine complex (I) can be used in an amount of 1/10,000 to 1/10 mole, and preferably 1/2,000 to 1/200 mole per mole of the substrate compound (IV).

In carrying out the present reaction, for example, the compound (IV) and the ruthenium-phosphine complex (I) are added to an appropriate solvent in a nitrogen atmosphere to obtain a homogeneous solution, which is then reacted for 5 to 150 hours, and preferably 7 to 50 hours under a hydrogen pressure of 10 to 150 atm, and preferably 20 to 100 atm at a reaction temperature of 10° to 100° C., and preferably 25° to 60° C.

Examples of the solvents used include alcohols such as methanol, ethanol, and isopropanol; halogenated compounds such as methylene chloride, 1,2-dichloroethane, and trichloroethylene; and ethers such as diethyl ether and diisopropyl ether. These solvents can be used singly or in combination.

Purification of the reaction product can be carried out by known methods including silica gel column chromatography and recrystallization (using a solvent such as diethyl ether, diisopropyl ether, benzene, and toluene).

The optically active 1-substituted-1,3-propanediol compound (III) thus obtained is a useful intermediate of, for example, pharmaceuticals. For example, optically active 1-phenyl-1,3-propanediol is an important synthetic intermediate of fluoxetine and tomoxetine useful as an antidepressant.

As explained above, the ruthenium-phosphine complex of the present invention is industrially useful as a catalyst excellent in enantioselectivity, and particularly in catalytic activity, which can be employed in organic synthetic reactions such as enantioselective synthetic reactions. In particular, when used as a catalyst for enantioselective hydrogenation of a 3-substituted-3-oxopropanol or a 3-substituted-3-oxopropanal, it produces a 1-substituted-1,3-propanediol useful as an intermediate of pharmaceuticals in high yield.

The present invention is now illustrated in greater detail with reference to Examples and Comparative Examples, but it should not be understood that the present invention is construed as being limited thereto. Each measurement of the present invention was undertaken on the following instruments and under the following conditions, unless otherwise noted.

$^1$H-NMR and $^{31}$P-NMR: Model AM-400 (400 MHz) (manufactured by Bruker, Inc.); Internal Standard: $^1$H-NMR . . . tetramethylsilane; External Standard: $^{31}$P-NMR . . . 85% phosphoric acid.

Optical Rotation: Model DIP-4 (manufactured by JASCO Inc.).

Optical Purity (High-performance Liquid Chromatography): Liquid Chromatograph: Hitachi L-6000 (manufactured by Hitachi Ltd.); Column: CHIRALCEL OB ($\phi$4.6 mm $\times$ 250 mm) (manufactured by Daicel Chemical Industries, Ltd.); Eluent: Hexane/Isopropanol (93/7 by volume); Flow Rate: 1 ml/min; Detector: UV Detector L-4000 (manufactured by Hitachi Ltd.) (UV-254 nm).

The abbreviations used in Examples and Comparative Examples are as follows.

BINAP: 2,2'-Bis(diphenylphosphino)-1,1'-binaphthyl

Tol-BINAP: 2,2'-Bis(di-p-tolylphosphino)-1,1'-binaphthyl

DM-BINAP: 2,2'-Bis[di(3,5-dimethylphenyl)phosphino]-1,1'-binaphthyl p-Cl-BINAP: 2,2'-Bis[di(p-chlorophenyl)phosphino]-1,1'-binaphthyl

EXAMPLE 1

Synthesis of [RuI(p-cymene) ((R)-BINAP)]I$_3$

In a 500 ml flask with side arm was charged 5.0 g (4.5 mmole) of [RuI(p-cymene)((R)-BINAP)]I in a nitrogen atmosphere, and 270 ml of methanol was added thereto, followed by stirring the mixture at room temperature for 30 minutes. Then, 30 ml of a methanol solution of 3.5 g (13.5 mmole) of iodine was added thereto, and the mixture was stirred at room temperature for 90 minutes. The precipitated crystal was collected by filtration and dried for 24 hours at room temperature under reduced pressure (1 mmHg) to give 5.9 g (percent yield: 96%) of the titled compound.

$^{31}$P-NMR (400 MHz, CDCl$_3$) $\delta$ ppm: 24.95 (d, J=59.8 Hz), 41.05 (d, J=59.6 Hz).

Elemental analysis for C$_{54}$H$_{46}$P$_2$RuI$_4$: Calcd. (%): C 47.50; H 3.40; Found (%): C 47.61; H 3.12.

Solubility: 1 g/5,700 ml (methanol, 25° C.) (The solubility of [RuI(p-cymene)((R)-BINAP)]I was 1 g/370 ml of methanol at 25° C.).

EXAMPLE 2

Synthesis of [RuI(p-cymene)((R)-Tol-BINAP)]I$_3$

The titled complex was obtained (percent yield: 97.5%) in the same manner as in Example 1, except for replacing (R)-BINAP with (R)-Tol-BINAP as a ligand.

$^{31}$P-NMR (400 MHz, CDCl$_3$) $\delta$ ppm: 23.36 (d, J=59.7 Hz), 39.31 (d, J=58.9 Hz).

Elemental analysis for C$_{58}$H$_{54}$P$_2$RuI$_4$: Calcd. (%) C 49.00; H 3.83; Found (%): C 48.72; H 3.63.

Solubility: 1 g/1,400 ml (methanol, 25° C.) (The solubility of [RuI(p-cymene)((R)-Tol-BINAP)]I was 1 g/95 ml of methanol at 25° C.).

EXAMPLE 3

Synthesis of [RuI(p-cymene)((R)-DM-BINAP)]I$_3$

The titled complex was obtained (percent yield: 94.3%) in the same manner as in Example 1, except for replacing (R)-BINAP with (R)-DM-BINAP as a ligand.

$^{31}$P-NMR (400 MHz, CDCl$_3$) $\delta$ ppm: 25.70 (d, J=58.7 Hz), 39.32 (d, J=58.9 Hz).

Elemental analysis for C$_{62}$H$_{62}$P$_2$RuI$_4$: Calcd. (%): C 50.39; H 4.23; Found (%): C 50.27; H 4.20.

EXAMPLE 4

Synthesis of [RuI(p-cymene)((R)-p-Cl-BINAP)]I$_3$

The titled complex was obtained (percent yield: 92.1%) in the same manner as in Example 1, except for replacing (R)-BINAP with (R)-p-Cl-BINAP as a ligand.

$^{31}$P-NMR (400 MHz, CDCl$_3$) $\delta$ ppm: 24.65 (d, J=59.7 Hz), 39.88 (d, J=59.8 Hz).

Elemental analysis for C$_{54}$H$_{42}$Cl$_4$P$_2$RuI$_4$: Calcd. (%): C 43.14; H 2.82; Found (%): C 43.02; H 2.61.

EXAMPLE 5

Enantioselective Hydrogenation of 3-Phenyl-3-oxopropanol

In a 500 ml stainless steel-made autoclave were charged 65 g (400 mmole) of 3-phenyl-3-oxopropanol and 550 mg (0.4 mmole) of [RuI(p-cymene)((R)-BINAP)]I$_3$ synthesized in Example 1 in a nitrogen atmosphere, and 300 ml of methanol was added thereto, followed by stirring the mixture at 30° C. for 20 hours under a hydrogen pressure of 30 atm. The reaction mixture was concentrated and subjected to silica gel column chromatography (eluent: hexane/isopropanol=9/1 by volume) to eliminate the complex. The obtained hydrogenation product was dissolved in a 6-fold amount of diisopropyl ether by heating and allowed to stand at 0° C. for 24 hours. The resulting precipitate was collected by filtration and dried (room temperature, 1 mmHg), and 45.5 g of (1S)-phenyl-1,3-propanediol was obtained as a colorless crystal (percent yield: 70.0%).

m.p.: 64.9° C.

$[\alpha]_D^{25}$: −41.2° (c=1.0, methanol).

$^1$H-NMR (400 MHz, CDCl$_3$) δ ppm: 1.88–2.03 (m, 2H), 2.88–3.02 (br s, 1H) 3.79–3.88 (m, 2H), 4.89–4.94 (m, 1H) 7.25–7.38 (m, 5H).

The obtained (1S)-phenyl-1,3-propanediol was subjected to high-performance liquid chromatography. As a result, it was found to have an optical purity of 99.9% ee.

REFERENCE EXAMPLE 1

Synthesis of Sodium Salt of 3-Phenyl-3-oxopropanal

In a 1,000 ml four-necked flask were charged 360 ml of dried toluene and 212 g (1.1 mole) of a 28% methanol solution of sodium methylate. The mixture was heated at 50° C., and 120 g (1.0 mole) of acetophenone and 111 g (1.5 mole) of ethyl formate were added thereto, followed by stirring the mixture at 50° C. for 20 hours. The resulting precipitate was collected by filtration and dried at 50° C. under reduced pressure (1 mmHg) for 6 hours to obtain 145 g of the desired sodium salt as a pale yellow crystal (percent yield: 85.3%).

$^1$H-NMR (400 MHz, D$_2$O) δ ppm: 7.40–7.72 (m, 6H), 9.02 (br s, 1H).

REFERENCE EXAMPLE 2

Synthesis of 3-Phenyl-3-oxopropanal

In a 200 ml four-necked flask were charged 25 ml of diisopropyl ether and 62.5 ml of 20% aqueous hydrochloric acid in a nitrogen atmosphere, followed by vigorously stirring the mixture at room temperature. Subsequently, 62.5 ml of an aqueous solution of 25.53 g (1.5 mmole) of the sodium salt prepared in Reference Example 1 was slowly added thereto, followed by vigorously stirring the mixture at room temperature for 1 hour. The reaction mixture was subjected to liquid separation in a nitrogen atmosphere, and the organic layer was washed with 25 ml of purified water. The desired 3-phenyl-3-oxopropanal was obtained as a diisopropyl ether solution. The titled compound was used in the subsequent reaction without being isolated and purified.

$^1$H-NMR (400 MHz, CDCl$_3$) δ ppm: 7.30–8.40 (m, 8H).

EXAMPLE 6

Enantioselective Hydrogenation of 3-Phenyl-3-oxopropanal

In a 200 ml stainless steel-made autoclave were charged 426.5 mg of [RuI(p-cymene)(R)-Tol-BINAP-]I$_3$ prepared in Example 2, the diisopropyl ether solution of 3-phenyl-3-oxopropanal prepared in Reference Example 2, 100 ml of methanol, and 2.0 ml of degassed purified water in a nitrogen atmosphere, followed by stirring the mixture at 50° C. for 22 hours under a hydrogen pressure of 50 atm. The reaction mixture was concentrated and subjected to silica gel column chromatography (eluent: hexane/isopropanol=9/1 by volume) to eliminate the complex. The obtained hydrogenation product was dissolved in a 6-fold amount of diisopropyl ether by heating and allowed to stand at 0° C. for 24 hours. The resulting precipitate was collected by filtration and dried (room temperature, 1 mmHg), and 10.5 g of (1S)-phenyl-1,3-propanediol was obtained as a colorless crystal (percent yield: 45%).

EXAMPLES 7 TO 10 AND COMPARATIVE EXAMPLES 1 TO 2

Enantioselective Hydrogenation of 3-Phenyl-3-oxopropanol (S)-1-Phenyl-1,3-propanediol was obtained in the same manner as in Example 5, except for changing the kind and amount of ruthenium-optically active phosphine complex, the hydrogen pressure, and the reaction time and for adding iodine, if desired. The reaction conditions and the results obtained are given in Table 1.

TABLE 1

| Example No. | Ruthenium-Optically Active Phosphine Complex | s/c[1] | Additive[2] | Hydrogen Pressure (atm) | Reaction Time (hr) | Conversion (%) | Chemical Purity (%) | Optical Purity (% ee) |
|---|---|---|---|---|---|---|---|---|
| 7 | [RuI(p-cymene) (R)-BINAP)]I$_3$ | 500 | | 100 | 20 | 97.6 | 97.2 | 87.6 |
| 8 | [RuI(p-cymene) (R)-BINAP)]I$_3$ | 1000 | | 100 | 20 | 89.2 | 97.2 | 86.4 |
| 9 | [RuI(p-cymene) (R)-BINAP)]I | 500 | Iodine (3) | 100 | 20 | 99.1 | 91.9 | 78.8 |
| 10 | [RuI(p-cymene) (R)-BINAP)]I | 1000 | Iodine (3) | 100 | 20 | 94.4 | 98.9 | 91.0 |
| Comparative Example 1 | [RuI(p-cymene) (R)-BINAP)]I | 100 | | 100 | 22.5 | 99.7 | 97.6 | 82.2 |
| Comparative Example 2 | [RuI(p-cymene) (R)-BINAP)]I | 500 | | 100 | 20.5 | 45.5 | 96.4 | 87.4 |

[1] The value of s/c represents a molar ratio of the substrate to the ruthenium-optically active phosphine complex.
[2] The number in the parenthesis represents a molar equivalent of the additive to the ruthenium-optically active phosphine complex.

What is claimed is:

1. A ruthenium-phosphine complex represented by formula (I):

[RuI(p-cymene)(R$^1$-BINAP)]I$_3$  (I)

wherein R$^1$-BINAP represents a tertiary phosphine represented by formula (II):

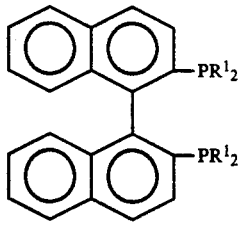
(II)

wherein $R^1$ represents a phenyl group which may be substituted with a lower alkyl group or a fluorine, chlorine, bromine or iodine atom at the p-position, the m-position or both the p-position and the m-position.

2. A ruthenium-phosphine complex as claimed in claim 1, wherein $R^1$-BINAP is an optically active tertiary phosphine.

3. A ruthenium-phosphine complex as claimed in claim 1, wherein $R^1$ is a phenyl group substituted with a chlorine atom.

4. A ruthenium-phosphine complex as claimed in claim 3, wherein $R^1$ is a p-chlorophenyl group.

5. A ruthenium-phosphine complex as claimed in claim 1, wherein $R^1$ is a phenyl group substituted with a lower alkyl group at the p-position.

6. A ruthenium-phosphine complex as claimed in claim 5, wherein $R^1$ is a p-tolyl group.

7. A ruthenium-phosphine complex as claimed in claim 1, wherein $R^1$ is a phenyl group substituted with a lower alkyl group at the m-position.

8. A ruthenium-phosphine complex as claimed in claim 7, wherein $R^1$ is a 3,5-dimethylphenyl group.

* * * * *